United States Patent
Bertram, III

(10) Patent No.: US 8,808,375 B2
(45) Date of Patent: Aug. 19, 2014

(54) ANTI-BACKOUT ARTHROSCOPIC UNI-COMPARTMENTAL PROSTHESIS

(75) Inventor: Morton Bertram, III, Naples, FL (US)

(73) Assignee: SurgenCo, LLC, Gulf Breeze, FL (US)

( * ) Notice: Subject to any disclaimer, the term of this patent is extended or adjusted under 35 U.S.C. 154(b) by 1693 days.

(21) Appl. No.: 12/049,674

(22) Filed: Mar. 17, 2008

(65) Prior Publication Data
US 2008/0183219 A1    Jul. 31, 2008

Related U.S. Application Data

(63) Continuation of application No. 10/738,652, filed on Dec. 17, 2003, now abandoned.

(51) Int. Cl.
*A61F 2/30* (2006.01)
*A61F 2/38* (2006.01)
*A61F 2/46* (2006.01)

(52) U.S. Cl.
CPC ............... *A61F 2/38* (2013.01); *A61F 2/4618* (2013.01); *A61F 2002/30759* (2013.01); *A61F 2/30756* (2013.01); *A61F 2/30767* (2013.01); *A61F 2/30771* (2013.01); *A61F 2/30965* (2013.01); *A61F 2002/30205* (2013.01); *A61F 2002/30327* (2013.01); *A61F 2002/30616* (2013.01); *A61F 2002/30878* (2013.01); *A61F 2002/30884* (2013.01); *A61F 2002/30892* (2013.01); *A61F 2002/3895* (2013.01); *A61F 2002/4635* (2013.01); *A61F 2230/0067* (2013.01); *A61F 2250/0039* (2013.01); *A61F 2310/00023* (2013.01); *A61F 2310/00029* (2013.01); *A61F 2310/00179* (2013.01); *A61F 2310/00796* (2013.01)

USPC ..................... 623/14.12; 623/20.16

(58) Field of Classification Search
USPC ............. 623/20.16, 20.34, 20.36, 14.12
See application file for complete search history.

(56) References Cited

U.S. PATENT DOCUMENTS

| | | | |
|---|---|---|---|
| 5,037,439 | A | 8/1991 | Albrektsson et al. |
| 5,122,144 | A | 6/1992 | Bert et al. |
| 5,219,362 | A | 6/1993 | Tuke et al. |
| 5,234,433 | A | 8/1993 | Bert et al. |
| 5,624,463 | A | 4/1997 | Stone et al. |
| 5,682,886 | A | 11/1997 | Delp et al. |
| 5,871,018 | A | 2/1999 | Delp et al. |
| 5,871,541 | A | 2/1999 | Gerber et al. |
| 6,007,496 | A | 12/1999 | Brannon |
| 6,290,726 | B1 | 9/2001 | Pope et al. |

(Continued)

FOREIGN PATENT DOCUMENTS

| | | | | |
|---|---|---|---|---|
| DE | 282 179 | A5 * | 9/1990 | ............ A61F 2/30 |
| EP | 0349173 | | 1/1990 | |

(Continued)

*Primary Examiner* — David H Willse
(74) *Attorney, Agent, or Firm* — Gifford, Krass, Sprinkle, Anderson & Citkowski, P.C.

(57) ABSTRACT

An improved uni-compartmental implant has a shaft having a proximal end attached to a head and a distal end, and one or more raised portions spaced apart along the shaft to resist back-out. The length between the head and distal end is preferably less than 50 mm, the distal end of the shaft has a diameter on the order of 2 to 3 mm, the proximal end of the shaft has a diameter on the order of 2 to 4 mm, and the head has a diameter ranging from 4 mm or less to 20 mm or more, making the device suitable for knee arthroscopy and other applications.

9 Claims, 1 Drawing Sheet

(56) References Cited

U.S. PATENT DOCUMENTS

| | | | |
|---|---|---|---|
| 6,299,644 | B1 | 10/2001 | Vanderschot et al. |
| 6,398,815 | B1 | 6/2002 | Pope et al. |
| 6,402,787 | B1 | 6/2002 | Pope et al. |
| 6,410,877 | B1 | 6/2002 | Dixon et al. |
| 6,425,922 | B1 | 7/2002 | Pope et al. |
| 6,468,314 | B2 * | 10/2002 | Schwartz et al. .......... 623/23.72 |
| 2002/0099446 | A1 | 7/2002 | MacArthur |

FOREIGN PATENT DOCUMENTS

| | | | | |
|---|---|---|---|---|
| EP | 0611560 | | 8/1994 | |
| EP | 0667134 | | 8/1995 | |
| EP | 0 845 964 B1 * | 1/2005 | ................ A61F 2/32 |
| FR | 2642301 | | 8/1990 | |
| FR | 2759896 | | 8/1998 | |
| GB | 2308068 | | 6/1997 | |
| WO | WO-9527450 | | 10/1995 | |
| WO | WO 97/25942 A1 * | 7/1997 | ................ A61F 2/32 |

* cited by examiner

ANTI-BACKOUT ARTHROSCOPIC UNI-COMPARTMENTAL PROSTHESIS

REFERENCE TO RELATED APPLICATION

This application is a continuation of U.S. patent application Ser. No. 10/738,652, filed Dec. 17, 2003, now abandoned, the entire content of which is incorporated herein by reference.

FIELD OF THE INVENTION

This invention relates generally to joint-related prosthetic devices and, in particular, to an arthroscopic, uni-compartmental prosthesis.

BACKGROUND OF THE INVENTION

Due in part to an aging population that wishes to remain active, arthritis of the knee is approaching epidemic proportions in the U.S. Another factor is obesity, since the knees bear much of increased weight in the body. It is estimated that approximately 750,000 surgical procedures are done in the U.S. each year for knee problems, including total-knee replacements, partial-knee replacements, and arthroscopic procedures.

Quite often, patients treated with knee arthroscopy for arthritis of the knee do very poorly. There are a number reasons for this, but the low rate of success is largely due to the fact that these patients have a small area of their cartilage which is denuded of cartilage and they continue to have pain. Although the area of cartilage eburnation is not large enough to warrant joint replacement procedure, it is large enough to cause continued problems and significant patient dissatisfaction.

Uni-compartmental knee procedures have therefore become more popular in recent years. One reason is that smaller incisions are now used, to the extent that uni-compartmental knees are now carried out through a so-called minimally invasive approach. Still, however, in many cases this involves a 4-inch incision, significant soft tissue dissection, and significant morbidity for the patient.

To improve these procedures, various implants and techniques are being devised. One of many is disclosed in Published U.S. Patent Application 2002/0099446 A1. This reference discloses a knee-joint prosthesis comprising at least one femoral component and at least one tibial component. The femoral component includes a first portion adapted for fixable attachment to a distal end of a femur and a second portion formed with a bearing surface. The femoral component is sized so as to permit attachment to the femur of a patient without severing at least one of the cruciate ligaments. The tibial component has a first surface that is adapted to cooperate with a patient's tibia, while a second surface of the tibial component is adapted to cooperate with the femoral component. The tibial component is sized so as to permit attachment to the patients tibia without severing at least one of the cruciate ligaments.

Despite advances such as these, however, the need remains for an improved implant, preferably one that resists back-out.

SUMMARY OF THE INVENTION

This invention resides in an improved uni-compartmental implant including a shaft having a proximal end attached to a head and a distal end, and one or more raised portions spaced apart along the shaft to resist back-out. The length between the head and distal end is preferably less than 50 mm, the distal end of the shaft has a diameter on the order of 2 to 3 mm, the proximal end of the shaft has a diameter on the order of 2 to 4 mm, and the head has a diameter ranging from 4 mm or less to 20 mm or more, making the device suitable for knee arthroscopy and other applications.

The shaft and/or raised portions may include a bone-ingrowth or bone-ongrowth surface, and the shaft and/or raised portions may be made of a fiber-metal. The head portion is preferably ceramic, though a chrome-cobalt alloy, titanium, or other bio-compatible material may be used. The head portion may have a bi-convex shape, a plano-convex shape, or a concave-convex shape.

DETAILED DESCRIPTION OF THE INVENTION

Figure 1:
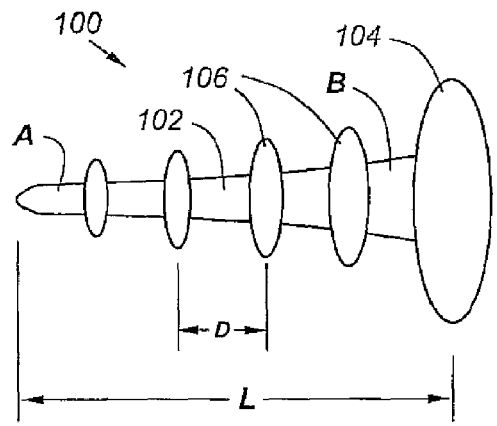
FIG. 1 is a drawing that illustrates a preferred embodiment of the invention.
Figure 2:
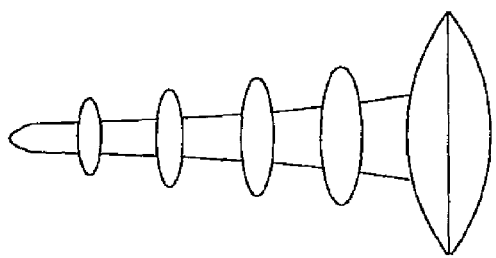
FIG. 2 is a drawing that illustrates an alternative head design.
Figure 3:
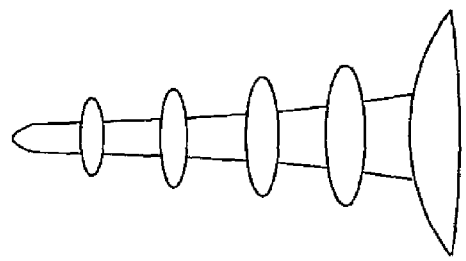
FIG. 3 is a drawing that illustrates a different alternative head design.
Figure 4:
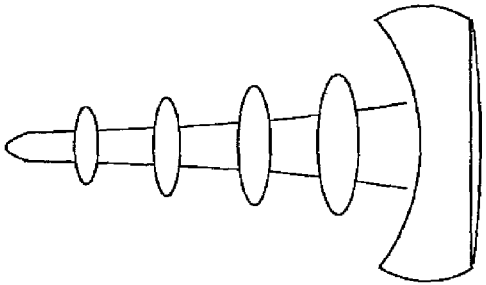
FIG. 4 is a drawing that illustrates yet a further alternative head design.
Figure 5:
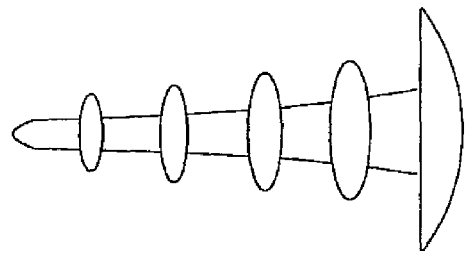
FIG. 5 is a drawing that illustrates yet a further, different alternative head design.

FIG. 1 illustrates a preferred embodiment of the invention. The implantable device, shown generally at 100, includes a shaft portion 102 having a head portion 104 and one or more raised portions 106 to resist pull-out. In terms of dimensions, the length of the device is preferably on the order of 25 mm, though length in excess of this, or on the order of 10 mm or less, may be more appropriate depending upon the application. The distance between the raised portions, "D" is preferably a few millimeters; for example, between 5 and 10 millimeters, depending upon the number used and other considerations.

The shaft portion 102 preferably tapers from a diameter at "B" of 3 mm, or less, to a diameter at "A" of 2.5 mm, or thereabouts. The head 104 will preferably be offered in different diameters, such as 4, 6, 8, 10, 15, and 20 mm, and so forth, in which case smaller-diameter heads may have smaller dimensions of A and B, and larger-diameter heads may have larger dimensions of A and B. Smaller dimensions may use less raised portions 106, whereas larger dimensions may use more of them.

Although the head portion 104 is generally shown as a bi-convex shape, other head geometries may be appropriate, such as plano-convex, concave-convex, and different radii of curvature, whether concave or convex surfaces are used. In addition, although the edge of the bi-convex surfaces of the head 104 are shown in the drawing as smoothly transitioning through a smaller radius, the sharp edge may alternatively be used. FIGS. 2-5 show three possible alternative head configurations.

In terms of materials, the head portion may be made of any appropriate bio-compatible material, such as chrome cobalt or titanium, though in the preferred embodiment, ceramic is used. The shaft 102 and raised portions 106 preferably include some type of porous ingrowth or ongrowth surface such as hydroxyapatite, and such surfaces may be used in conjunction with raised bumps to further assist in preventing backout. Although a metallic shaft in raised portions may be used, when available, a fiber metal one is the preferred technology.

The inventor has also devised a way to perform a procedure arthroscopically without large incisions so that we could take care of these patchy areas of eburnated bone within an isolated condyle in the knee. The procedure could be done on the lateral or medial side, and if the technique was altered slightly, it could even be applied to the patellofemoral groove. The technique would involve a variation of a procedure known as the OATS procedure. In this procedure, osteoarticular transfer of tissue is performed by using essentially a trephine to core out a plug of bad bone where the cartilage has been worn away or eburnated and then an area of the knee is harvested that has articular cartilage covering it but is not needed, for instance, the inner portion of the patellofemoral groove or inner portion of the medial and lateral femoral condyle along the intercondylar notch. These tissue plugs, which contain bone and cartilage, are then transferred over to this area. This procedure has had moderate success. It is mostly used for young people who have isolated articular defects.

According to this invention, the OATS procedure is converted to an arthroplasty technique where, instead of a plug of bone and cartilage, the plug of FIG. 1 is instead used. The area of defect would be isolated, identified, and measured, then a guide wire would be placed centrally into the defect. Over the guide wire, a cannulated reamer would be placed that we would ream to a specified depth. This would establish the canal size for the 'stem' of the prosthesis. We would then over-ream with a secondary reamer which would then establish the size for the 'rounded head' of the prosthesis. At this point, the prosthesis could be either press fitted or cemented into place in the defect.

I believe that this technique would have significant advantages over the OATS procedure since this would be more rigidly fixed and it would be sealing the defect with cement and/or cobalt chrome. It would be more applicable for the elderly population as they have more of a geographic eburnation of bone as opposed to small circumscribed lesions that are applicable to the OATS procedure. I would envision that for a typical arthritic knee, one would need multiple plugs of cobalt chrome that could be placed in these areas. With relative ease, the surgeon could place as many as four or five of these circular plugs in the knee to take care of the eburnated areas where the bone is exposed. An inventory would be maintained that would come in different diameter sizes and stem lengths for the prostheses. They could easily be used in a right or a left knee and each prosthesis implanted would be a separate charge. They are relatively small; therefore, they would not occupy a large amount of shelf space at the hospital or in the local distributors office. The instrumentation would be easy to design and would fit very nicely in a self-contained unit.

In rare situations, we would find eburnated bone on the tibial side. This would obviously be more difficult to reach because of the anatomy of the knee. However, it is conceivable that lesions within the anterior two-thirds of the knee on the tibial plateau could easily be re-surfaced in a manner such as I just described. These plugs will actually be more flat as opposed to a slightly rounded plug that would be used on the femoral side.

I claim:

1. An arthroscopic surgical procedure for treating a defect in a knee joint having a femoral side with medial and lateral condylar protrusions on respective sides of a patellofemoral groove and a tibial side with a platform against which the condylar protrusions articulate, the method comprising the steps of:
    identifying a region of eburnated bone associated with a knee joint;
    measuring the region;
    providing an implant having a shaft and a head with dimensions corresponding to the measured region, the head having a first side attached to the shaft and an opposing second side having a convex outer surface;
    reaming a central portion of the region to a specific depth corresponding to the shaft of the implant;
    over-reaming with a secondary reamer corresponding to the size of the head of the implant;
    press fitting or cementing the implant into the reamed and over-reamed portion of the defect; and
    wherein the implant has a single, tapered shaft having a central longitudinal axis.

2. An arthroscopic surgical procedure for treating a defect in a knee joint having a femoral side with medial and lateral condylar protrusions on respective sides of a patellofemoral groove and a tibial side with a platform against which the condylar protrusions articulate, the method comprising the steps of:
    identifying a region of eburnated bone associated with a knee joint;
    measuring the region;
    providing an implant having a shaft and a head with dimensions corresponding to the measured region, the head having a first side attached to the shaft and an opposing second side having a convex outer surface;
    reaming a central portion of the region to a specific depth corresponding to the shaft of the implant;
    over-reaming with a secondary reamer corresponding to the size of the head of the implant;
    press fitting or cementing the implant into the reamed and over-reamed portion of the defect; and wherein:
    the implant has a single, tapered shaft having a central longitudinal axis; and
    a plurality of separate raised portions spaced apart along the shaft to resist back-out.

3. An arthroscopic surgical procedure for treating a defect in a knee joint having a femoral side with medial and lateral condylar protrusions on respective sides of a patellofemoral groove and a tibial side with a platform against which the condylar protrusions articulate, the method comprising the steps of:
    identifying a region of eburnated bone associated with a knee joint;
    measuring the region;
    providing an implant having a shaft and a head with dimensions corresponding to the measured region, the head having a first side attached to the shaft and an opposing second side having a convex outer surface;
    reaming a central portion of the region to a specific depth corresponding to the shaft of the implant;
    over-reaming with a secondary reamer corresponding to the size of the head of the implant;
    press fitting or cementing the implant into the reamed and over-reamed portion of the defect; and wherein:
    the implant has a single, tapered shaft having a central longitudinal axis; and
    a plurality of separate raised portions spaced apart along the shaft to resist back-out, each raised portion forming a continuous, uninterrupted band extending outwardly from the shaft.

4. An arthroscopic surgical procedure for treating a defect in a knee joint having a femoral side with medial and lateral condylar protrusions on respective sides of a patellofemoral groove and a tibial side with a platform against which the condylar protrusions articulate, the method comprising the steps of:
   identifying a region of eburnated bone associated with a knee joint;
   measuring the region;
   providing an implant having a shaft and a head with dimensions corresponding to the measured region, the head having a first side attached to the shaft and an opposing second side having a convex outer surface;
   reaming a central portion of the region to a specific depth corresponding to the shaft of the implant;
   over-reaming with a secondary reamer corresponding to the size of the head of the implant;
   press fitting or cementing the implant into the reamed and over-reamed portion of the defect; and wherein:
   the implant has a single, tapered shaft having a central longitudinal axis;
   a plurality of separate raised portions spaced apart along the shaft to resist back-out, each raised portion forming a continuous, uninterrupted band extending outwardly from the shaft; and
   each raised portion lying on a separate plane perpendicular to the longitudinal axis and becoming successively smaller from the proximal end to the distal end.

5. An arthroscopic surgical procedure for treating a defect in a knee joint having a femoral side with medial and lateral condylar protrusions on respective sides of a patellofemoral groove and a tibial side with a platform against which the condylar protrusions articulate, the method comprising the steps of:
   identifying a region of eburnated bone associated with a knee joint;
   measuring the region;
   providing an implant having a shaft and a head with dimensions corresponding to the measured region, the head having a first side attached to the shaft and an opposing second side having a convex outer surface;
   reaming a central portion of the region to a specific depth corresponding to the shaft of the implant;
   over-reaming with a secondary reamer corresponding to the size of the head of the implant;
   press fitting or cementing the implant into the reamed and over-reamed portion of the defect; and
   wherein the length of the implant is less than 50 mm.

6. An arthroscopic surgical procedure for treating a defect in a knee joint having a femoral side with medial and lateral condylar protrusions on respective sides of a patellofemoral groove and a tibial side with a platform against which the condylar protrusions articulate, the method comprising the steps of:
   identifying a region of eburnated bone associated with a knee joint;
   measuring the region;
   providing an implant having a shaft and a head with dimensions corresponding to the measured region, the head having a first side attached to the shaft and an opposing second side having a convex outer surface;
   reaming a central portion of the region to a specific depth corresponding to the shaft of the implant;
   over-reaming with a secondary reamer corresponding to the size of the head of the implant;
   press fitting or cementing the implant into the reamed and over-reamed portion of the defect; and
   wherein the shaft has a diameter on the order of 2 to 4 mm.

7. An arthroscopic surgical procedure for treating a defect in a knee joint having a femoral side with medial and lateral condylar protrusions on respective sides of a patellofemoral groove and a tibial side with a platform against which the condylar protrusions articulate, the method comprising the steps of:
   identifying a region of eburnated bone associated with a knee joint;
   measuring the region;
   providing an implant having a shaft and a head with dimensions corresponding to the measured region, the head having a first side attached to the shaft and an opposing second side having a convex outer surface;
   reaming a central portion of the region to a specific depth corresponding to the shaft of the implant;
   over-reaming with a secondary reamer corresponding to the size of the head of the implant,
   press fitting or cementing the implant into the reamed and over-reamed portion of the defect; and
   wherein the head is ceramic.

8. An arthroscopic surgical procedure for treating a defect in a knee joint having a femoral side with medial and lateral condylar protrusions on respective sides of a patellofemoral groove and a tibial side with a platform against which the condylar protrusions articulate, the method comprising the steps of:
   identifying a region of eburnated bone associated with a knee joint;
   measuring the region;
   providing an implant having a shaft and a head with dimensions corresponding to the measured region, the head having a first side attached to the shaft and an opposing second side having a convex outer surface;
   reaming a central portion of the region to a specific depth corresponding to the shaft of the implant;
   over-reaming with a secondary reamer corresponding to the size of the head of the implant;
   press fitting or cementing the implant into the reamed and over-reamed portion of the defect; and
   wherein the head is constructed of a chrome-cobalt alloy or other bio-compatible alloy.

9. An arthroscopic surgical procedure for treating a defect in a knee joint having a femoral side with medial and lateral condylar protrusions on respective sides of a patellofemoral groove and a tibial side with a platform against which the condylar protrusions articulate, the method comprising the steps of:
   identifying a region of eburnated bone associated with a knee joint;
   measuring the region;
   providing an implant having a shaft and a head with dimensions corresponding to the measured region, the head having a first side attached to the shaft and an opposing second side having a convex outer surface;
   reaming a central portion of the region to a specific depth corresponding to the shaft of the implant;
   over-reaming with a secondary reamer corresponding to the size of the head of the implant;
   press fitting or cementing the implant into the reamed and over-reamed portion of the defect; and
   wherein the head has a diameter ranging from 2 mm to 20 mm.

* * * * *